(12) United States Patent
Agrawal

(10) Patent No.: US 6,489,304 B2
(45) Date of Patent: *Dec. 3, 2002

(54) HYPERSTRUCTURE-FORMING CARRIERS

(75) Inventor: Sudhir Agrawal, Shrewsbury, MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 166 days.

(21) Appl. No.: 08/846,879

(22) Filed: May 1, 1997

(65) Prior Publication Data

US 2001/0006945 A1 Jul. 5, 2001

(51) Int. Cl.$^7$ .............................................. A61K 31/70
(52) U.S. Cl. ..................... 514/44; 435/320.1; 435/91.4; 435/455
(58) Field of Search .................. 435/6, 455, 320.1, 435/91.4; 514/44; 536/23.1

(56) References Cited

U.S. PATENT DOCUMENTS 5,952,490 A * 9/1999 Hanecak et al. ........... 536/24.5

FOREIGN PATENT DOCUMENTS

| WO | WO 93/1312 | * | 8/1993 |
| WO | WO 94/08053 | * | 4/1994 |
| WO | WO 94/25037 | * | 11/1994 |

OTHER PUBLICATIONS

Stull et al. IPharmaceutical Res. Vil. 12, 4, 1995, 465–483, 1995.*
Agrawal et al., PNAS, vol. 85, 1988, 7079–7083.*
Scaringe et al., Nucleic acid Res, vol. 18, 18, 5433, 1990.*
Uhlmann et al. Chemical Reviews, vol. 90, 4, 1990.*

* cited by examiner

Primary Examiner—Dave T. Nguyen
(74) Attorney, Agent, or Firm—Hale and Dorr LLP

(57) ABSTRACT

Disclosed are bioactive substances useful for the delivery of effector units in animals. Also disclosed are methods for utilizing the bioactive substances of the invention.

11 Claims, 14 Drawing Sheets

5'-CTCTCGCACCCATCTCTCCTTCTGGGG-3'
    └─────── EFFECTOR UNIT ──────┘└─────┘
                                  HYPERSTRUCTURE
                                  FORMING UNIT
                                  (HFU)

5'-CTCTCGCACCCATCTCTCCTTCTGTGT-3'
    └─────── EFFECTOR UNIT ──────┘└─────┘
                                  HYPERSTRUCTURE
                                  FORMING UNIT
                                  (HFU)

FIG. 1B

HYPERSTRUCTURE-FORMING CARRIERS

BACKGROUND OF THE INVENTION

1. Field of the Invention

This invention relates to the delivery of bioactive substances. In particular, the invention relates to the delivery of effector units in animals, and to the modulation of their release.

2. Summary of the Related Art

Drugs are compounds almost always foreign to the body. The processes of inputting, distributing and eliminating drugs are therefore of paramount importance in determining the onset, duration and intensity of drug effect. Hence, in the context of drug development, the ability to modulate the rate at which a particular drug becomes systemically available, and to direct its bioavailability to a particular tissue are often of crucial significance. Pharmakokinetic, pharmacological and toxological constraints create the need to modulate drug delivery to minimize side effects or to optimize drug efficacy.

Drug delivery involves both drug absorption (the process of movement from the site of administration toward systemic circulation) and drug distribution or bioavailability (the process by which a drug becomes available at the site of action. Direct placement of a drug into the bloodstream (usually i.v.) ensures complete delivery of the dose to the general circulation only. Because drug distribution to other tissues is often delayed, direct administration may result in the accumulation of high plasma concentrations of the drug administered immediately postinfusion. Notably, high plasma concentrations (beyond the therapeutic window for a particular drug regiment) often cause a wide variety of toxic drug reactions which are dose-related. In addition, for many drugs and/or metabolites, distribution to the active site or tissue necessitate movement across biological barriers, for example via passive diffusion, facilitated diffusion or pinocytosis. For most drugs, distribution is not limited to the desired site (i.e., the site of action) thereby reducing their efficacy and increasing the chances of undesirable side effects.

Therefore, there is a need to develop delivery systems and methods suitable to control drug release following administration and to direct drug diffusion through biological barriers in a selective fashion. Gene therapy, and more specifically antisense therapy, is emblematic of a promising pharmacological approach for which there is a pressing need to control drug release and direct drug delivery to particular sites of action.

The potential for using oligonucleotides as inhibitors of specific gene expression in an antisense therapeutic approach was first suggested in the late '70s. (Paterson et al., Proc. Natl. Acad. Sci. USA 74: 4370–4374 (1977); Zamecnik and Stephenson, Proc. Natl. Acad. Sci. USA 75: 280–284 and 285–288 (1978)). To date, the ability of antisense oligonucleotides to inhibit virus propagation has become firmly established. (See e.g., Agrawal, Trends in Biotechnology 10: 152–158 (1992). Antisense oligonucleotides have also been developed as anti-parasitic agents. (See e.g., PCT publication no. WO93/13740; Tao et al., Antisense Research and Development 5: 123–129 (1995)). More recently, antisense oligonucleotides have shown promise as candidates for therapeutic applications for diseases resulting from expression of cellular genes. (See e.g., PCT publication no. WO95/09236, PCT publication no. WO94/26887, and PCT application no. PCT/US94/13685). The development of various antisense oligonucleotides as therapeutic and diagnostic agents has recently been reviewed by Agrawal and Iyer, Current Opinion in Biotechnology 6: 12–19 (1995).

Much is currently being discovered about the pharmacodynamic properties of oligonucleotides. Agrawal et al., Clinical Pharmacokinetics 28: 7–16 (1995) and Zhang et al., Clinical Pharmacology and Therapeutics 58: 44–53 (1995). Some of these new studies have led to new challenges to be overcome for the optimization of oligonucleotides as therapeutic agents. Such optimization should include elimination or reduction of cardiovascular side effects and in vivo instability problems. Henry et al., Pharm. Res. 11: PPDM8082 (1994) discloses that oligonucleotides may potentially interfere with blood clotting. Cardiovascular side effects are believed to stem from high plasma concentrations of oligonucleotides which have been observed immediately postinfusion. Effective in vivo stability of oligonucleotides is affected by both their degradation and their elimination. With respect to in vivo stability of oligonucleotides, it has been shown that following intravenous administration to mice, rats or monkeys, oligonucleotides are degraded mainly from the 3'- end. (Temsamani et al., Antisense and Nucleic Acid Drug Development (in press)). Notably, because of instability considerations, higher dosages of oligonucleotides are necessary. Gailbraith et al., Antisense Research and Development 4:201–206 (1994) discloses complement activation and depletion by phosphorothioate oligonucleotides. Recently, several studies on elimination of oligonucleotides have been published. Agrawal et al., Proc. Natl. Acad. Sci. (USA) 88: 7595–7599 (1991) describes the intravenous and intraperitoneal administration of a 20 mer phosphorothioate linked-oligonucleotide to mice. In this study, approximately 30% of the administered dose was excreted in the urine over the first 24 hours with accumulation preferentially in the liver and kidney. Plasma half-lives ranged from about 1 hour ($t_{1/2}\alpha$) and 40 hours ($t_{1/2}\beta$), respectively. Similar results have been reported in subsequent studies (Iversen, Anti-Cancer Drug Design 6:531–538 (1991); Iversen, Antisense Res. Devel. 4:43–52 (1994); and Sands, Mol. Pharm. 45:932–943 (1994)).

Dehydration and elimination of many other drugs may also affect their efficacy and therapeutic window. Therefore, there remains a need to develop more effective therapeutic methods for modulating the release and direct the delivery of drugs which can be easily manipulated to fit the animal and condition to be treated while producing fewer side effects.

SUMMARY OF THE INVENTION

This invention relates to bioactive substances with enhanced pharmakokinetic properties and to their use in biomedical applications. In particular, the invention relates to substances including carriers for the delivery of effector units in animals, and for the modulation of the release of the same. The present inventor has discovered that bioreversible association of a bioactive substance with a hyperstructure forming unit allows modulated release and directed delivery of the bioactive substance. Thus, the invention provides compounds and methods for modulating the release and direct the delivery of drugs which can be easily manipulated to fit the animal and condition to be treated while producing fewer side effects.

In a first aspect, the invention provides a bioactive substance including a hyperstructure forming unit and an effector unit, wherein there is an operable association between the hyperstructure forming unit and the effector unit.

In a preferred embodiment, the bioactive substance is an oligonucleotide including the bioreversibly attached nucleic acid sequence GGGG or GTGT capable of aggregating with other oligonucleotides in such a way as to assemble hyperstructures of two or more oligonucleotides.

In a second aspect, the invention provides methods for delivering the effector units of this invention. In a preferred embodiment of this aspect, the invention provides a method for delivering an effector unit in an animal, including a human, comprising administering to the animal a therapeutically effective amount of a bioactive substance according to the present invention, for a therapeutically effective period of time.

In a third aspect, the invention provides a method for investigating the biochemical and biophysical roles of particular genes. In the method according to this aspect of the invention, a bioactive substance with a nucleic acid sequence complementary to a target sequence of interest, is introduced in the cell type of interest. The bioactive substance of this invention can be administered at different points in the cell cycle, or in conjunction with promoters or inhibitors of cell growth to determine the role of the target sequence in the growth of the cell type of interest.

BRIEF DESCRIPTION OF THE DRAWINGS

FIG. 1B is a diagramatic representation of examples of some additional bioactive substances according to the present invention. The figure shows representative HFUs each in operable association with some representative, effector units.

DETAILED DESCRIPTION OF THE PREFERRED EMBODIMENTS

Figure 1A:
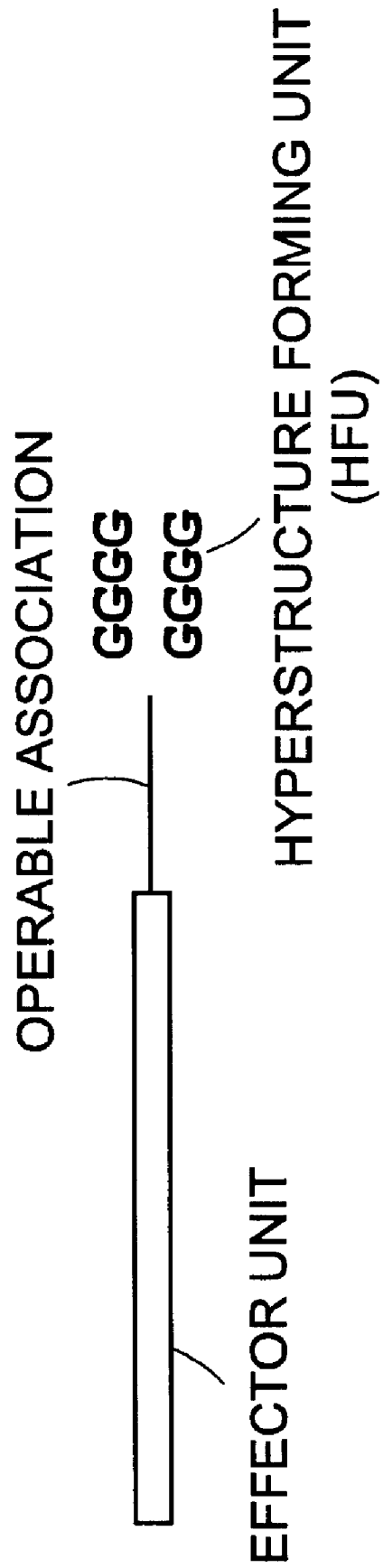
FIG. 1A is a diagramatic representation of an example of one embodiment of a bioactive substance according to the present invention. The figure shows a hyperstructure forming unit (HFU) in operable association with an effector unit.

This invention relates to substances for the delivery of effector units in animals. In addition, the invention provides methods for using such bioactive substances as analytical diagnostic tools, as potentiators of transgenic plant and animal studies and gene therapy approaches, and as potential therapeutic agents. The present inventor has discovered that bioreversible association of a bioactive substance with a hyperstructure forming unit allows modulated release and directed delivery of the bioactive substance. Thus, the invention provides compounds and methods for modulating the release and directing the delivery of drugs which can be easily manipulated to fit the condition to be treated while producing fewer side effects. The patents and scientific literature referred to herein establish the knowledge of those with skill in the art and are hereby incorporated by reference in their entirety.

In a first aspect the invention provides a bioactive substance including a hyperstructure forming unit, an effector unit and an operable association between the hyperstructure forming unit and the effector unit.

The term "bioactive substance", as used herein, denotes a biochemical moiety suitable as a means for the delivery of effector units in an animal including a human. The bioactive substance of this invention comprises at least a hyperstructure forming unit, an effector unit, and an operable association between the hyperstructure forming unit and the effector unit.

For therapeutic use, the bioactive substance according to the invention may optionally be formulated with any of the well known pharmaceutically acceptable carriers or diluents. This formulation may further contain one or more additional effector or it may contain any other pharmacologically active agent.

For purposes of the invention "hyperstructure forming unit" (also designated as HFU) refers to a biochemical moiety capable of associating with one or more additional hyperstructure forming units to establish a biolabile hyperstructure. Preferably, the hyperstructure forming unit is an oligonucleotide acid sequence.

In a preferred embodiment, the bioactive substance is an oligonucleotide including the sequence GGGG or GTGT capable of aggregating with other oligonucleotides in such a way as to assemble hyperstructures of two or more oligonucleotides.

In one preferred embodiment, the hyperstructure forming unit comprises an oligonucleotide sequence GTGT. In another preferred embodiment, the hyperstructure forming unit comprises an oligonucleotide sequence, GGGG. Guanosine clusters form an exceptionally stable parallel-stranded tetramer in which four layers of guanosine quartets are ordered in a helical array. (Sen and Gilbert, Nature 334:364–366 (1988)). Clusters of guanosine residues have been found in the telomeres of most eukaryotes. (Guschlbauer et al., J. Biomol. Struct. Dyn. 8:491–511 (1990)). Groups of four guanosine residues or guanosine quartets have been postulated to play a role in the integrity of chromosomal telomeres. (see e.g., Henderson et al., Cell 51:899–908 (1987); Williamson et al., Cell 59:871–880 (1989); Sandquist and Klug, Nature 342:825–829 (1989)). In each quartet each base is believed to be both the donor and the acceptor of two hydrogen bonds with its neighbor residue. Several guanosine quartets in turn may stack upon each other to form quadruple-helical structures with a guanosine quartet core which function to preserve the integrity of chromosomal telomeres. (Williamson, Current Opinion in Structural Biology 3:357–362 (1993)). In a preferred embodiment, the GTGT or GGGG nucleoside quartets have exclusively phosphodiester internucleoside linkages.

In another preferred embodiment, one HFU comprises an oligonucleotide sequence, preferably of from about 6 to about 10 nucleotides. A second HFU comprises another oligonucleotide sequence complementary in a Watson-Crick sense to the first HFU, and a third HFU comprises another oligonucleotide sequence complementary in a Hoogstein sense to the first or second HFU. The hyperstructure formed by this embodiment is a triple helix. In a preferred embodiment, the GTGT or GGGG nucleoside quartets have exclusively phosphodiester internucleoside linkages.

In one preferred embodiment, the bioactive substance includes a first and a second hyperstructure forming unit.

As used herein, the term "effector unit" denotes an active moiety capable of altering a biochemical state. The term effector unit therefore includes, without limitations, drugs or metabolites. Examples of such effector units include any substance used in the prevention, diagnosis, alleviation, treatment or cure of a pathological state. The term also includes any substance used to alter physical functions, systems or organs of the animal treated.

In one embodiment, the effector unit may include at least a nucleotide. The term nucleotide is used to denote a deoxyribonucleoside, a ribonucleoside, or a 2'-O-substituted ribonucleoside residue. In another embodiment, the effector unit comprises a nucleotidic portion. For purposes of the invention, the term "nucleotidic portion" includes polymers of two or more deoxyribonucleosides, ribonucleosides, or 2'-O-substituted ribonucleoside residues, or any combination thereof. Preferably, such nucleotidic portions have from about 8 to about 100 nucleoside residues, and most preferably from about 12 to about 30 nucleoside residues. The nucleotidic portion of the effector unit according to this embodiment may be partially or fully complementary to a target nucleic acid sequence. For purposes of the invention, "complementary" means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of the modulation of a specific gene expression. Alternatively, the nucleotide portion may comprise a ribozyme, an antisense oligonucleotide, an aptamer or a cytokine-inducing sequence, such as an unmethylated CpG sequence. The term "aptamer" designates a molecule whose activity depends on its tertiary structure.

The nucleosides of the nucleotidic portions are preferably stabilized by having nucleosides coupled to each other by any of the numerous known non-phosphodiester internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain preferred embodiments, these internucleoside linkages may be phosphotriester, phosphorothioate, or phosphoramidate linkages, or combinations thereof. The term nucleotidic portion also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

The nucleotidic portion of the effector unit according to another embodiment could be chimeric, or hybrid, or chimeric and hybrid. The term "chimeric" designates a nucleic acid moiety attached via more than one type of internucleoside linkage. One preferred embodiment of such a chimeric nucleotidic portion comprises a phosphorothioate, phosphodiester or phosphorodithioate region, preferably comprising from about 2 to about 12 nucleotides, and an alkylphosphonate or alkylphosphonothioate region. Preferably, such chimeric nucleotidic portions contain at least three consecutive internucleoside linkages selected from phosphodiester and phosphorothioate linkages, or combinations thereof.

For purposes of the invention, "hybrid" refers to an nucleotidic portion having more than one type of nucleoside. One preferred embodiment comprises a ribonucleotide or 2'-O-substituted ribonucleotide region, preferably comprising from about 2 to about 12 2'-O-substituted nucleotides, and a deoxyribonucleotide region. Preferably, such a hybrid nucleotidic portion will contain at least three consecutive deoxyribonucleosides and will also contain ribonucleosides, 2'-O-substituted ribonucleosides, or combinations thereof.

Nucleotidic portions according to the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)).

Bioactive substances comprising an effector unit, including a nucleotidic portion according to the invention, are useful for a variety of purposes. For example, they can be used as "probes" of the physiological function of a particular target sequence in an experimental cell culture or animal system, and to evaluate the effect of inhibiting such gene activity. This is accomplished by administering to a cell or to an animal a bioactive substance according to the invention and observing any phenotypic effects. In this use, nucleotidic portions of the effector unit according to the invention are preferable to traditional "gene knockout" approaches because they are easier to use and can be used to inhibit a target sequence activity at selected stages of development or differentiation. Thus, effectors units according to the invention can serve as probes to test the role of a particular target gene sequence in various stages of development.

Finally, effector units containing nucleotidic portions according to the invention, are useful in therapeutic approaches to benign and malignant tumors and other human diseases involving suppression of gene expression.

In yet another embodiment, the effector unit includes an amino acid. For purposes of this invention, the term "amino acid" is used to denote an organic acid in which one of the hydrogen atoms or a carbon atom has been replaced by the radical —$NH_2$. In one preferred embodiment the amino acid is an aminocarboxylic acid. In one particularly preferred embodiment, the effector unit is a peptide, most preferably comprising from about 3 to about 20 amino acids. In another embodiment, the effector unit is a tissue specific peptide including a tissue specific receptor binding peptide.

In another embodiment, the effector unit includes a lipid. For purposes of the invention, the term "lipid" is used to denote biological amphiphiles including fatty acids, acylglycerols, phosphoglycerides, sphingolipids, aliphatic alcohols, waxes, steroids, and any combination with other classes of compounds, such as protein or carbohydrate.

In yet another embodiment the effector unit includes a small molecule drug. The term "small molecule drug" is used to denote traditional pharmaceutical compounds (see e.g., Physician's Desk Reference, Medical Economics Company, Montvale, N.J. (1996).

Figure 2A:
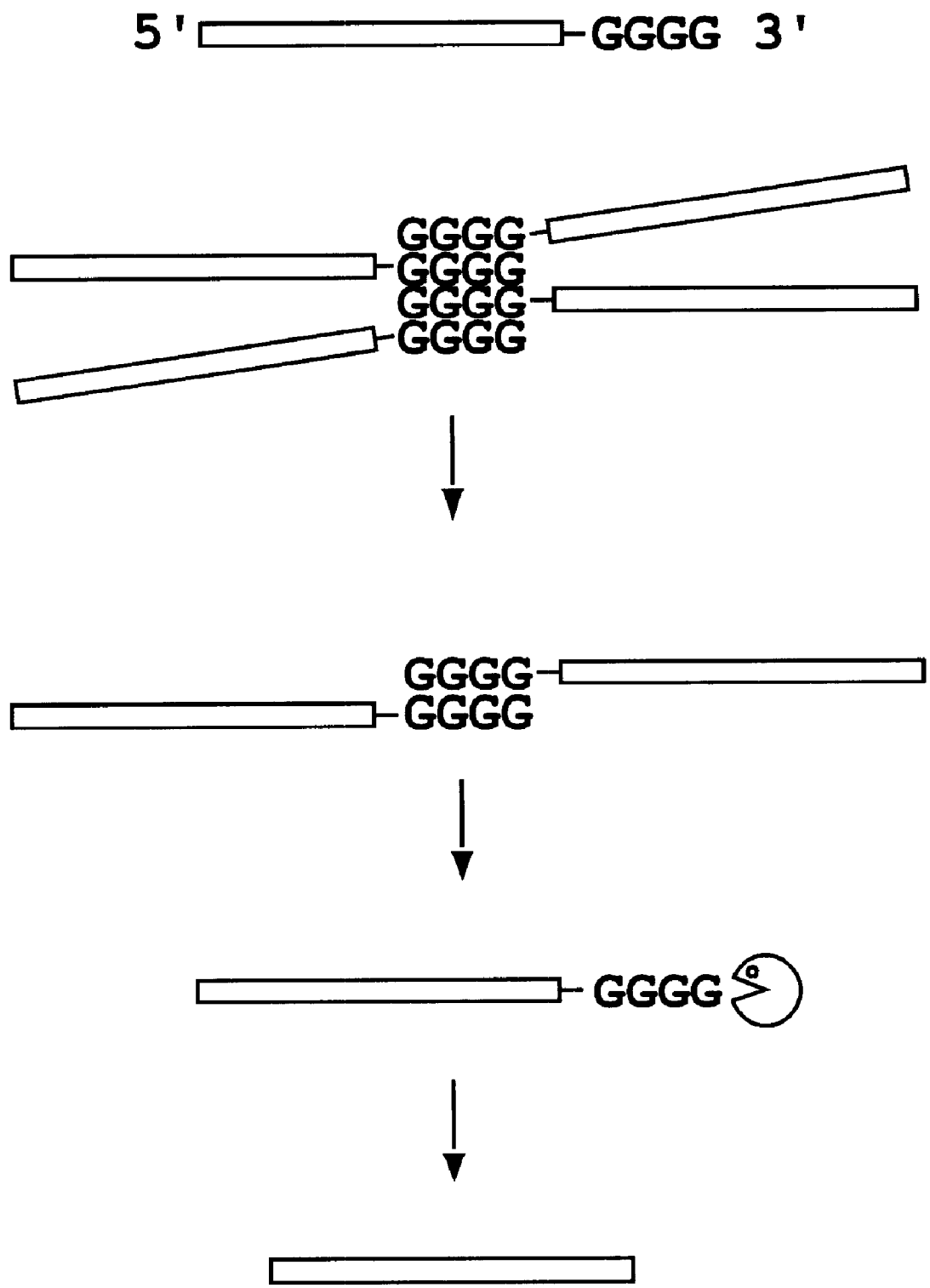
FIG. 2A is a diagramatic representation of a preferred embodiment of the invention showing the ability of HFUs to form hyperstructures comprising more than one bioactive substance. The figure also shows the disassembly of the hyperstructure and the subsequent release of the bioactive substance.
Figure 2B:
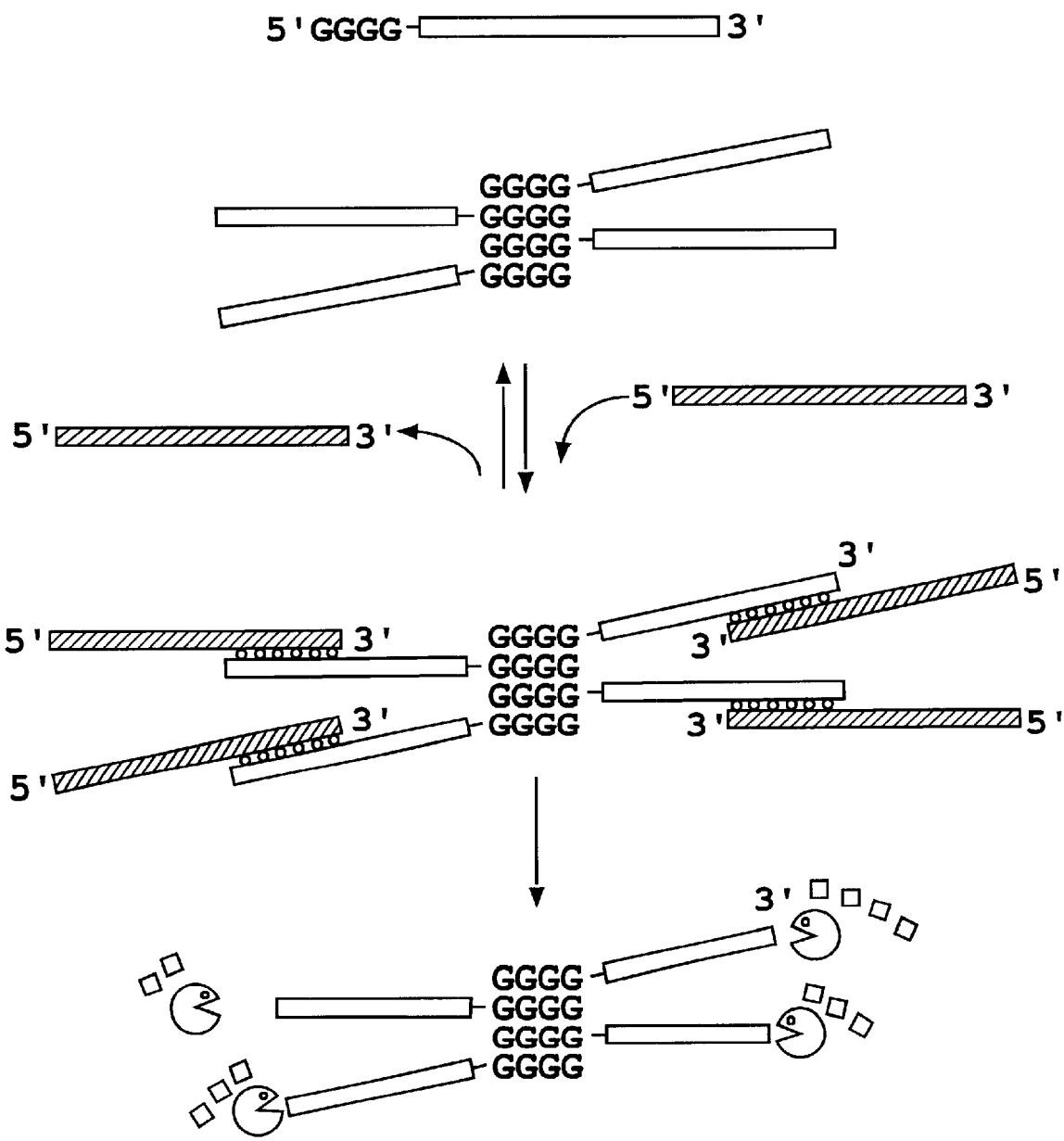
FIG. 2B is a diagramatic representation of another preferred embodiment of the invention in which the HFU and the effector unit are in indirect operable association.

For purposes of the invention "operable association" is used to denote a bioreversible association between the hyperstructure forming unit and the effector unit such that the two are brought in proximity of each other. (See FIG. 1). Such association may be direct or indirect (e.g., involving additional units). In an additional embodiment, the effector unit is in operable association with two or more effector units. (FIGS. 2A and 2B).

The operable association according to the present invention is bioreversible. Bioreversible, as used herein, denotes that the mammal has the ability to weaken or terminate the operable association such as to release the effector unit. As a practical matter, bioreversal of the operable association can be inferred from the observation of the specific effects attributable to the activity of the effector unit. Bioreversal can therefore be obtained by a suitable agent capable for example of cleaving the operable association of the particular embodiment. The latter depends on the biochemical nature of the operable association. Preferred examples of bioreversable operable association include, without limitation, ester linkages, which are cleaved by esterases, amide linkages, which are cleaved by amidases and disulfide linkages, which are cleaved by reduction of the disulfide bond. For example, in a preferred embodiment where the operable association is a phosphodiester bond between a nucleotide of the nucleotidic effector unit and a nucleotide of the hyperstructure forming unit, bioreversal may be achieved using an endonuclease. Alternatively, in such an embodiment, the HFU may contain exclusively phosphodiester bonds and be located at an end of the effector unit, thereby allowing its removal by an exonuclease. Particularly preferred operative associations are provided by an amide, disulfide or ester bond between an oligonucleotide HFU and a nucleotidic effector unit which has been stabilized as described previously, particularly wherein the HFU is located at either or both ends of the nucleotide effector unit.

In a second aspect, the invention provides methods for delivering the bioactive substance of this invention to a specific tissue. In an embodiment of this aspect, the invention provides a method for delivering an effector unit in an animal, including a human, comprising administering to the animal a therapeutically effective amount of a bioactive substance according to the present invention, for a therapeutically effective period of time. In the method according to this aspect of the invention, the bioactive substance may include a modulator unit.

The terms "delivery", "deliver" or "delivering" as used herein, includes both absorption, i.e., the process of movement from the site of administration toward systemic circulation, and distribution or bioavailability, i.e., the process by which a bioactive substance becomes available at the specific site(s) of action.

The terms "therapeutically effective amount" and "therapeutically effective period of time" are used to denote known treatments at dosages and for periods of time effective to achieve the therapeutic result sought. In a particularly preferred embodiment, control release of the effector unit is obtained by administering the bioactive substance according to this aspect of the invention by i.v., intramuscular or subcutaneous administration.

According to another embodiment, one or more bioactive substances of the invention may be administered to an animal either sequentially or simultaneously in a therapeutically effective amount and for a therapeutically effective period of time.

In a third aspect, the invention provides a method for investigating the biochemical and biophysical properties of specific sequences under tight regulation. In the method according to this aspect of the invention, the effector unit of the bioactive substance according to the invention, including a target sequence of interest, is introduced in the cell type of interest. The bioactive substance can be administered at different points in the cell cycle, or in conjunction with promoters or inhibitors of cell growth to determine the role of the target sequence in the growth of the cell type of interest.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLE 1

Bioactive Substance Preparation

To carry out in vivo pharmacokinetic studies of the bioactive substance of this invention, three PS-oligonucleotides were synthesized. All three PS-oligonucleotides have a common 25-mer PS-oligonucleotide sequence; the difference is in four additional nucleotides. Oligonucleotide HYB0411 (having the sequence 5'-CTCTCGCACCCATCTCTCTCCTTCTGGGG-3' (SEQ ID NO:1)) contains four contiguous guanosines, -GGGG- at the 3'-end; oligonucleotide H4B0412 (having the sequence 5'-CTCTCGCACCCATCTCTCTCCTTCTGTGT-3' (SEQ ID NO:2)) contains -GTGT- at the 3'-end; oligonucleotide H4B0413 (having the sequence 5'-CTCTCGCACCCATCTCTCTCCTTCT-3' (SEQ ID NO:3)) contains only the common 25-mer PS-oligonucleotide sequence. Oligonucleotide HYB0413 is a control sequence and does not contain contiguous guanosines.

Synthesis of the three PS-oligonucleotides was carried out using standard phosphoramidites chemistry on a 10 µM scale. Oligonucleotides were purified by reversed phase high performance liquid chromatography (Agrawal, *Trends in Biotech,* 14:376–387 (1996)).

EXAMPLE 2

Bioactive Substance Administration

To carry out pharmacokinetic studies, [$^{35}$S]-labeled PS-oligonucleotides were synthesized using phosphoramidite chemistry; the intermediate phosphite linkage was oxidized with [$^{35}$S$_8$] to incorporate [$^{35}$S]. (Agrawal, et al., Synthetic Methods for the Radioisotopic Labeling of Oligonucleotides, in: Antisense Oligonucleotide from Technology to Therapy (Schlingensiepen, ed.) Blackwell, Berlin, pp. 60–77 (1996)). [$^{35}$S] was incorporated at the fifth (oligonucleotide HYB0411) or fourth (oligonucleotide HYB0412 and HYB0413) internucleotide linkage.

A dose of 10 mg/kg of [$^{35}$S]-labeled PS-oligonucleotide was administered intravenously (i.v.) to rats (Wistar rats from Charles River, Wilmington, Mass.). Following administration, plasma was collected after 5, 15 and 30 minutes and after 1, 3, 6, 12, 24 and 48 hours. Radioactivity levels were measured to monitor plasma clearance at each time point. Following administration of PS-oligonucleotide, animals (3 rats/group) were sacrificed at 12, 24 and 48 hours. The following tissues were removed and homogenized: muscle, lung, liver, kidney, and spleen. Radioactive levels were measured, to monitor tissue distribution of each of the oligonucleotides. To follow the excretion of PS-oligonucleotides, urine and feces were collected using metabolism cages at 0–3, 3–6, 6–12, 12–24 and 24–48 hour intervals and radioactivity levels were measured using the methods previously reported (Zhang, et al., *Biochem. Pharmacol.,* 49: 929–939 (1995)).

Figure 3:
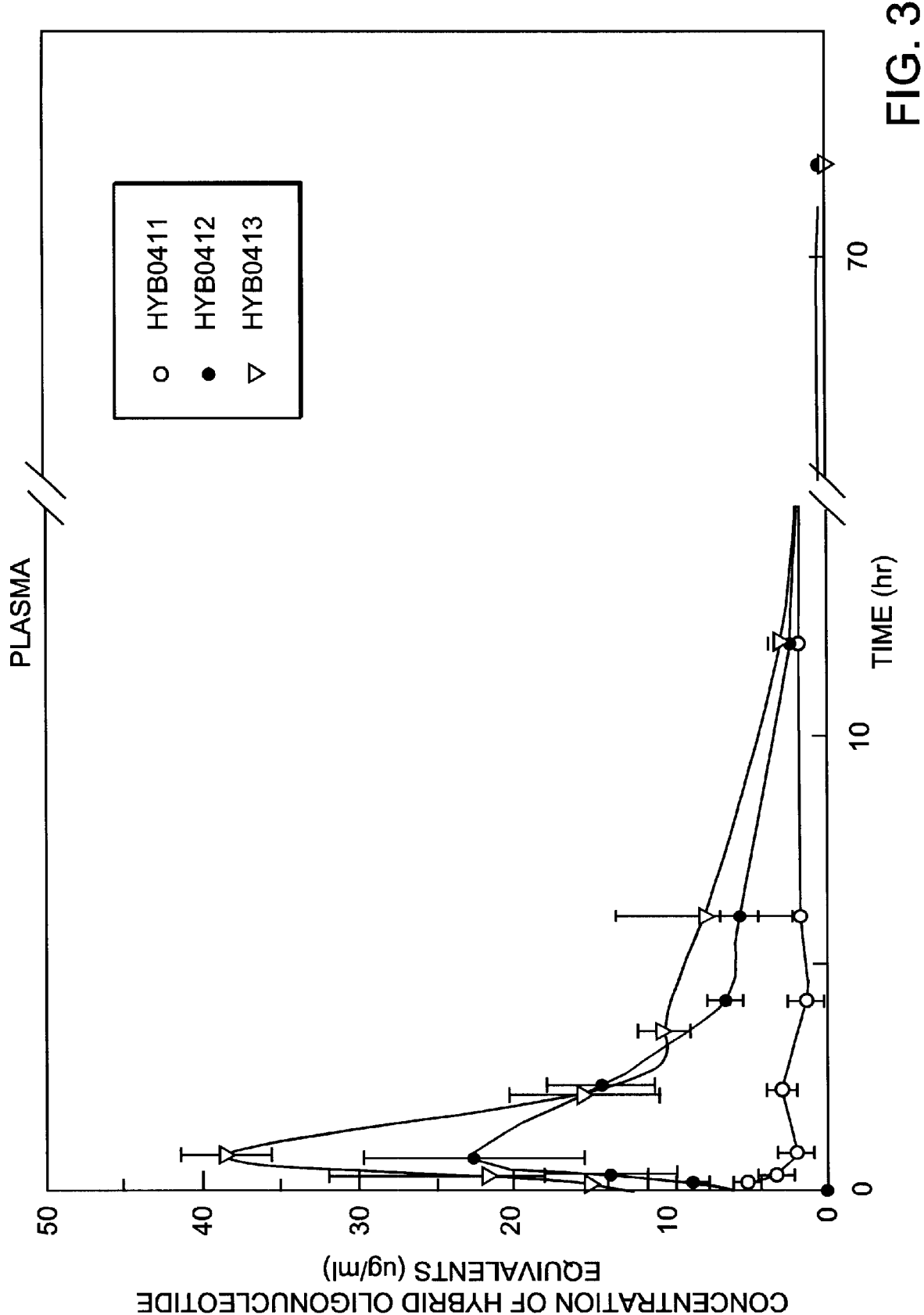
FIG. 3 is a diagramatic representation showing the plasma concentration-time course for a preferred embodiment of the invention in which the HFU and the effector unit are an oligonucleotide. The results are shown as oligonucleotide equivalents after i.v. bolus administration of radiolabeled oligonucleotides into rats, based on quantification of radioactivity.
Figure 4:
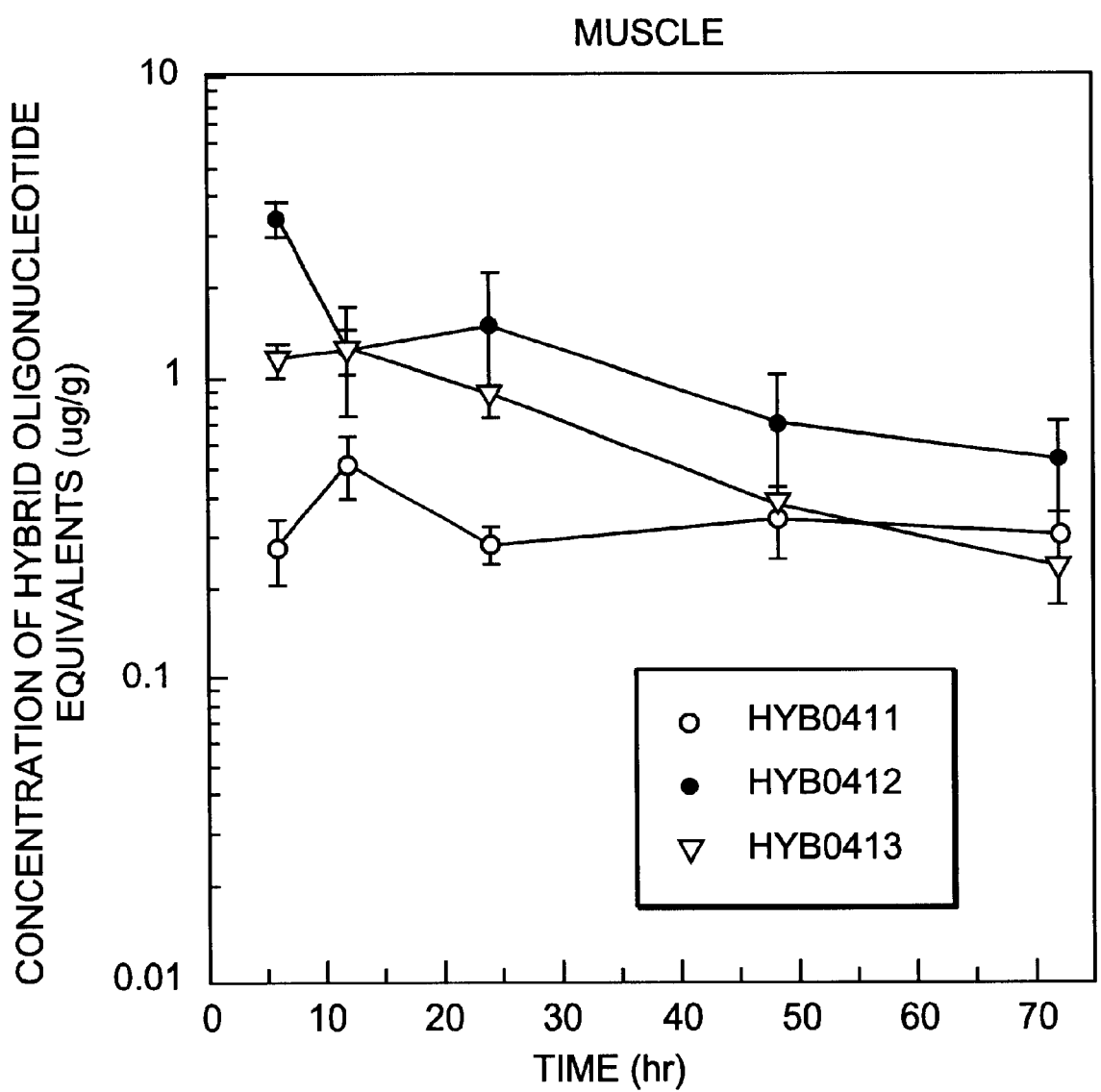
FIG. 4 is a diagramatic representation showing concentration-time courses in muscle tissue for a preferred embodiment of the invention in which the HFU and the effector unit are an oligonucleotide. The results are shown as oligonucleotide equivalents after i.v. bolus administration of radiolabeled oligonucleotides into rats, based on quantification of radioactivity.
Figure 5:
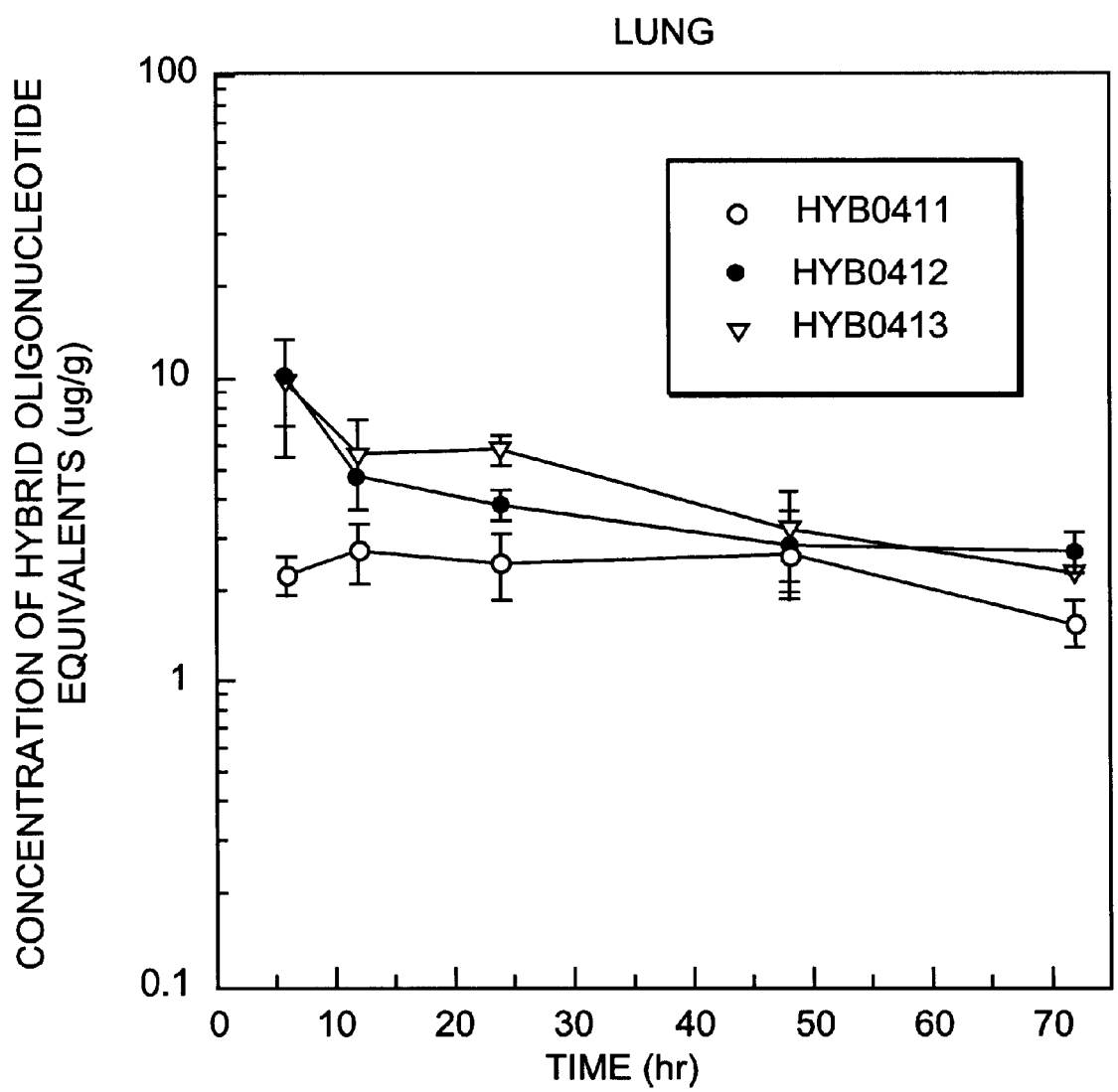
FIG. 5 is a diagramatic representation showing concentration-time courses in lung tissue for a preferred embodiment of the invention in which the HFU and the effector unit are an oligonucleotide. The results are shown as oligonucleotide equivalents after i.v. bolus administration of radiolabeled oligonucleotides into rats, based on quantification of radioactivity.
Figure 6:
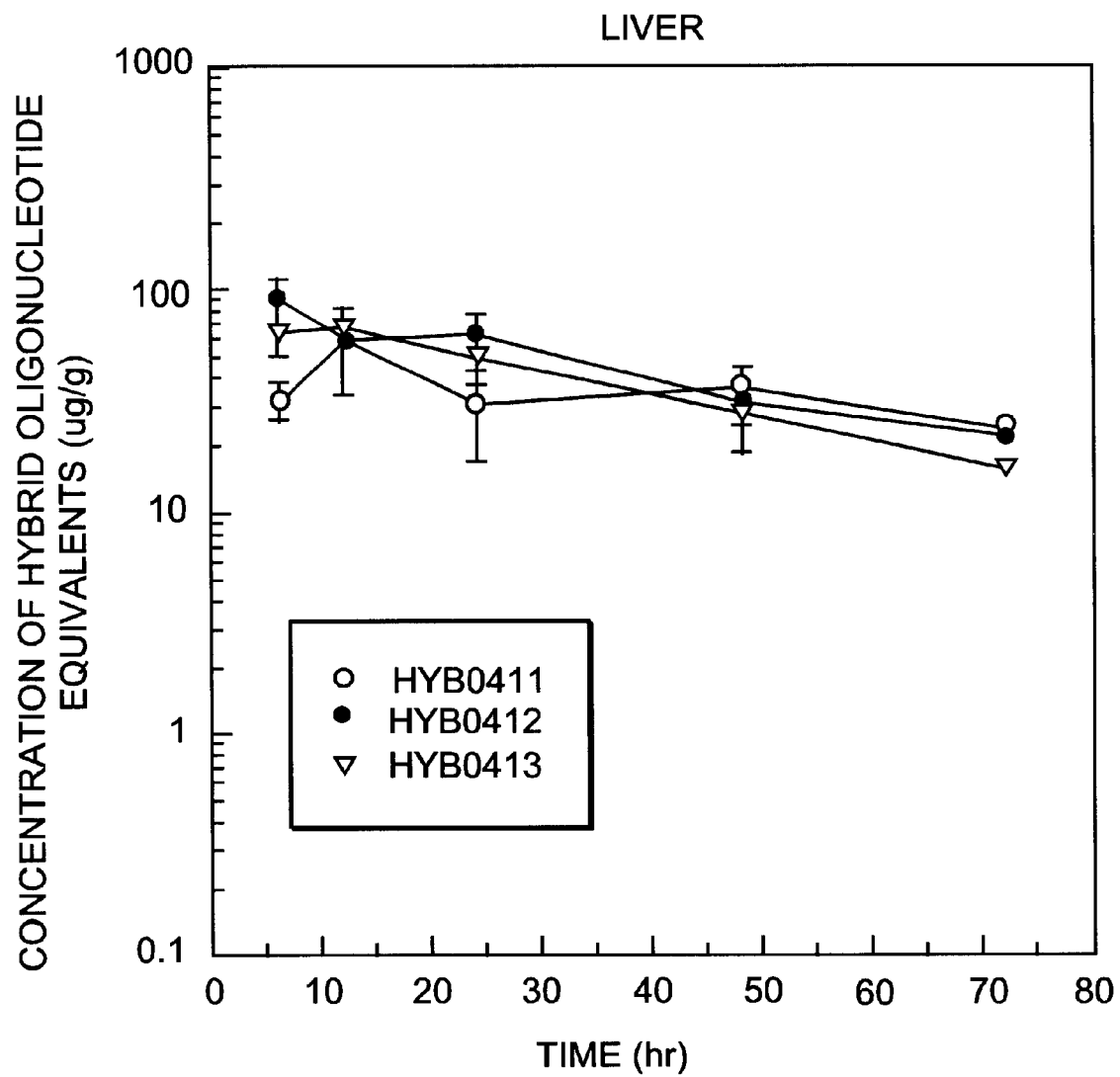
FIG. 6 is a diagramatic representation showing concentration-time courses in hepatic tissue for a preferred embodiment of the invention in which the HFU and the effector unit are an oligonucleotide. The results are shown as oligonucleotide equivalents after i.v. bolus administration of radiolabeled oligonucleotides into rats, based on quantification of radioactivity.
Figure 7:
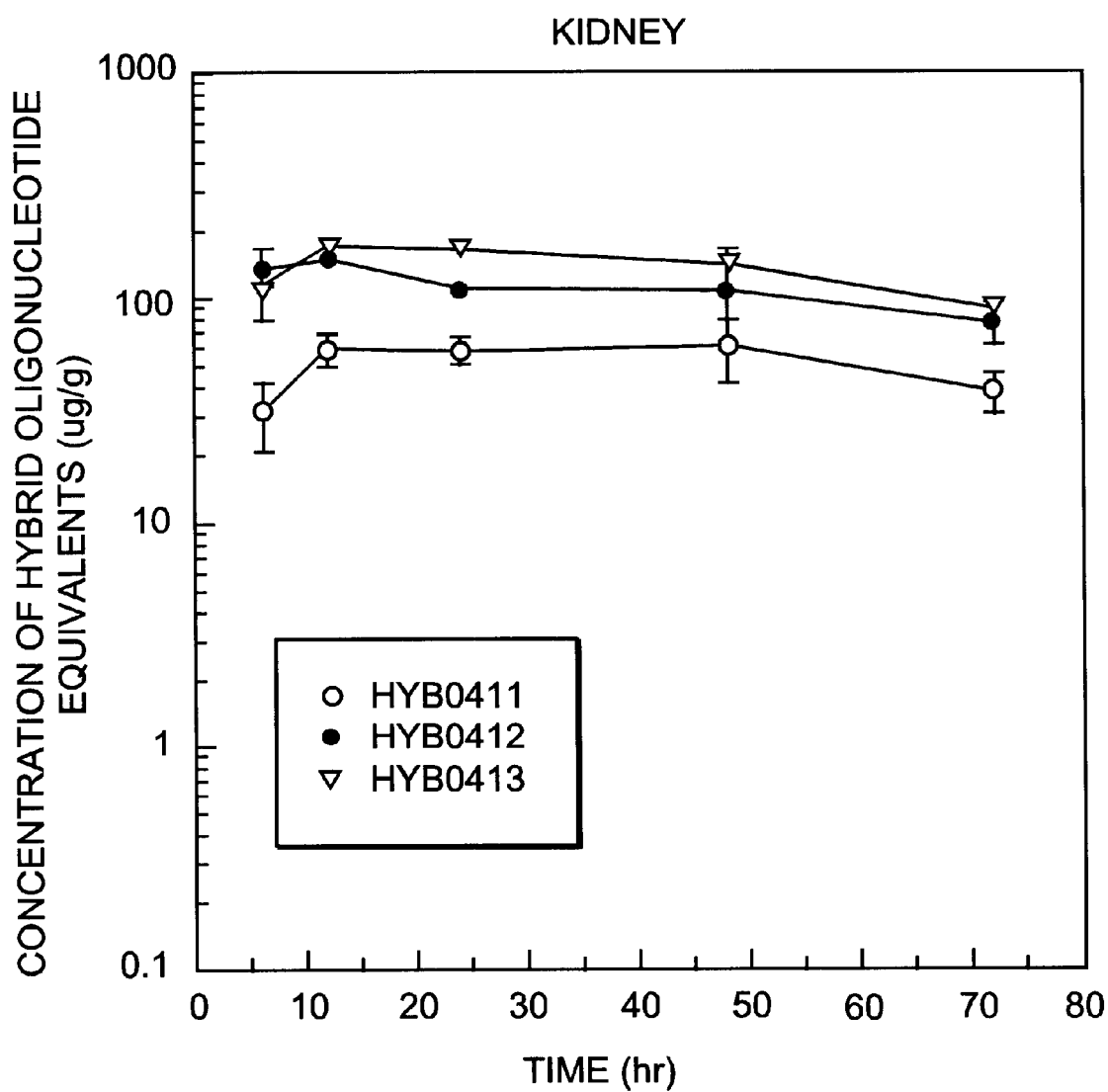
FIG. 7 is a diagramatic representation showing concentration-time courses in kidney for a preferred embodiment of the invention in which the HFU and the effector unit are an oligonucleotide. The results are shown as oligonucleotide equivalents after i.v. bolus administration of radiolabeled oligonucleotides into rats, based on quantification of radioactivity.
Figure 8:
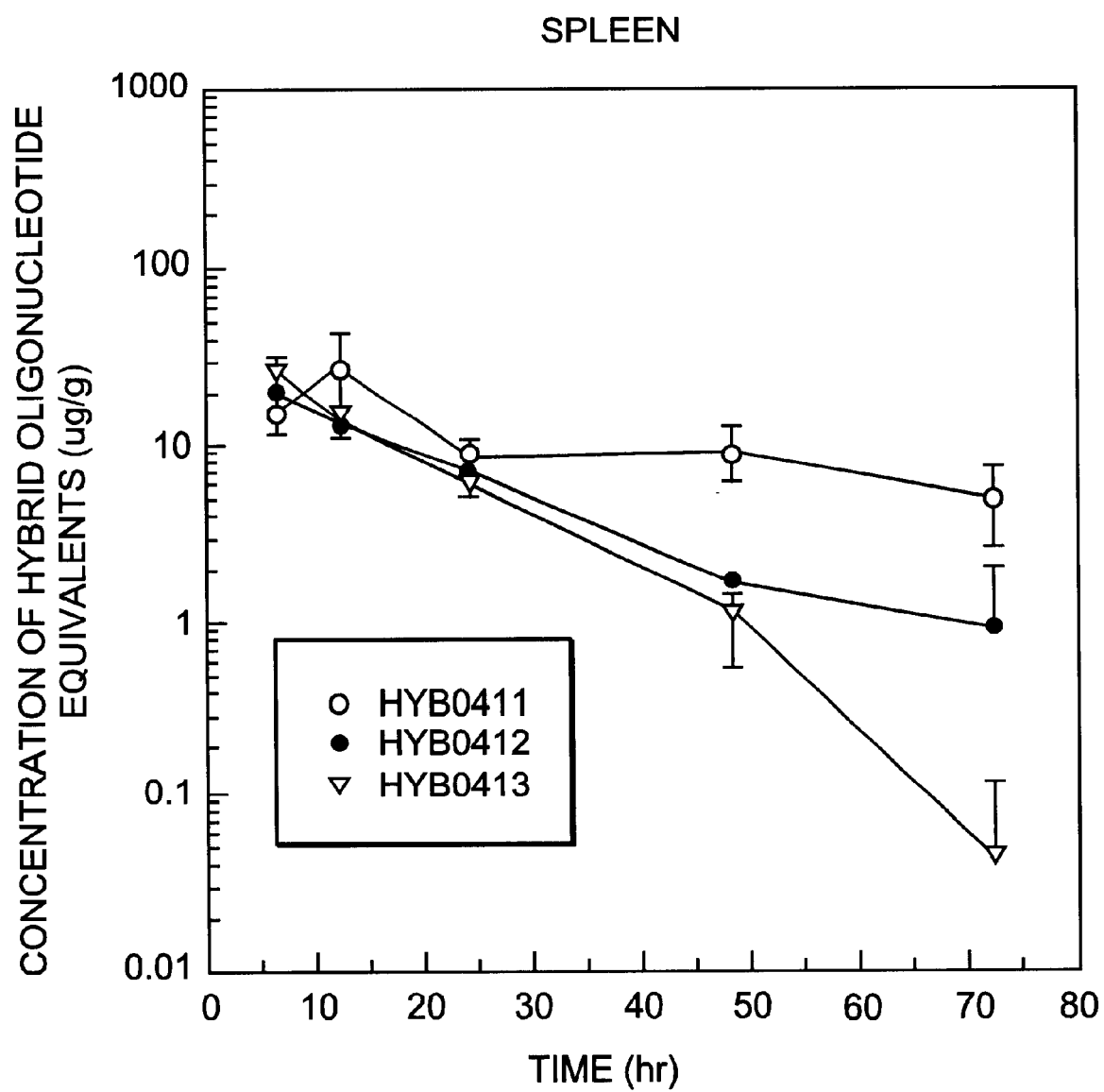
FIG. 8 is a diagramatic representation showing concentration-time courses in spleen tissue for a preferred embodiment of the invention in which the HFU and the effector unit are an oligonucleotide. The results are shown as oligonucleotide equivalents after i.v. bolus administration of radiolabeled oligonucleotides into rats, based on quantification of radioactivity.

FIG. 3 illustrates the plasma concentration-time courses of oligonucleotide equivalents after i.v. bolus administration of radiolabeled oligonucleotides into rats, based on quantification of radioactivity. As shown in previous studies (Agrawal, et al., *Clin. Pharm.* 28:7–16 (1995); Zhang, et al., *Biochem. Pharmacol.,* 49: 929–939 (1995)), PS-oligonucleotides rapidly clear from the plasma. Pharmacokinetic analysis revealed that plasma disappearance curves for oligonucleotide-derived radioactivity could be described by the sum of two exponentials, with a short distribution half-life and a long elimination half-life. Oligonucleotides HYB0411 and HYB0412 have significantly higher maximum plasma concentrations ($C_{max}$) than Oligonucleotide HYB0413. Oligonucleotide HYB0411 displayed a shorter distribution half-life ($t_{1/2}\alpha$) than did Oligonucleotide HYB0412 and Oligonucleotide HYB0413. No significant difference in plasma elimination half-life ($t_{1/2}\beta$) was observed. These results suggest that modification of PS-oligonucleotides with contiguous guanosines significantly affects plasma clearance of the molecules.

EXAMPLE 3

Bioactive Substance Distribution Analysis

The oligonucleotide-equivalent concentrations of radioactivity in tissues after i.v. bolus administration of radiolabeled oligonucleotides to rats are shown in FIGS. 4–8. As with other PS-oligonucleotides (Agrawal, et al., *Clin. Pharm.* 28:7–16 (1995); Zhang, et al., *Biochem. Pharmacol.,* 49: 929–939 (1995); Cossum, et al., *J. Pharm. Exp. Ther.,* (USA) 267:1181–1190 (1993)), the three oligonucleotides had a wide tissue distribution. Significant differences in distribution pattern were found among the three oligonucleotides. In general, Oligonucleotide HYB0411 and Oligonucleotide HYB0412 had similar tissue concentrations in the tissues examined; concentrations of Oligonucleotide HYB0413 were different from those of Oligonucleotide HYB0411 and Oligonucleotide HYB0412. Oligonucleotide HYB0411 had the highest kidney concentration: 40% higher than that of Oligonucleotides HYB0412 and HYB0413. Oligonucleotides HYB0411 and HYB0412 were present at approximately 50% higher concentrations in the liver than was Oligonucleotide HYB0413. Oligonucleotides HYB0411 and HYB0412 were present at 30% to 50% higher concentrations in the spleen than was Oligonucleotide HYB0413. Oligonucleotide HYB0413 was present in bone marrow at higher concentrations than Oligonucleotide HYB0411 and Oligonucleotide HYB0412 at 12 hours after dosing (data not shown). In the lung, however, Oligonucleotide HYB0413 was present in significantly higher concentrations than Oligonucleotide HYB0411 and Oligonucleotide HYB0412.

Figure 9:
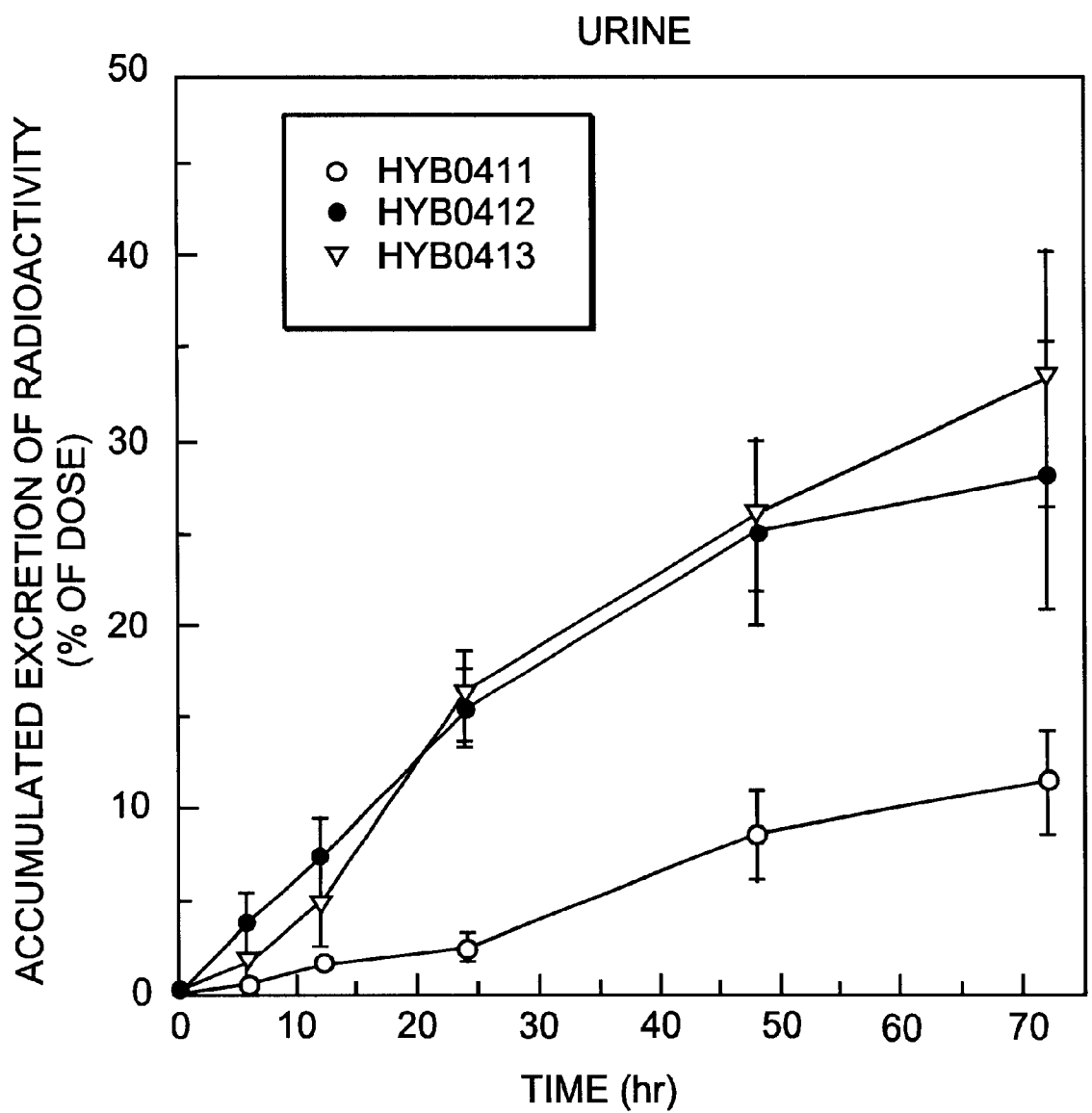
FIG. 9 shows the cumulative excretion of urinary radioactivity over a 48-hour period postinfusion of the radiolabeled bioactive substance according to the present invention.
Figure 10:
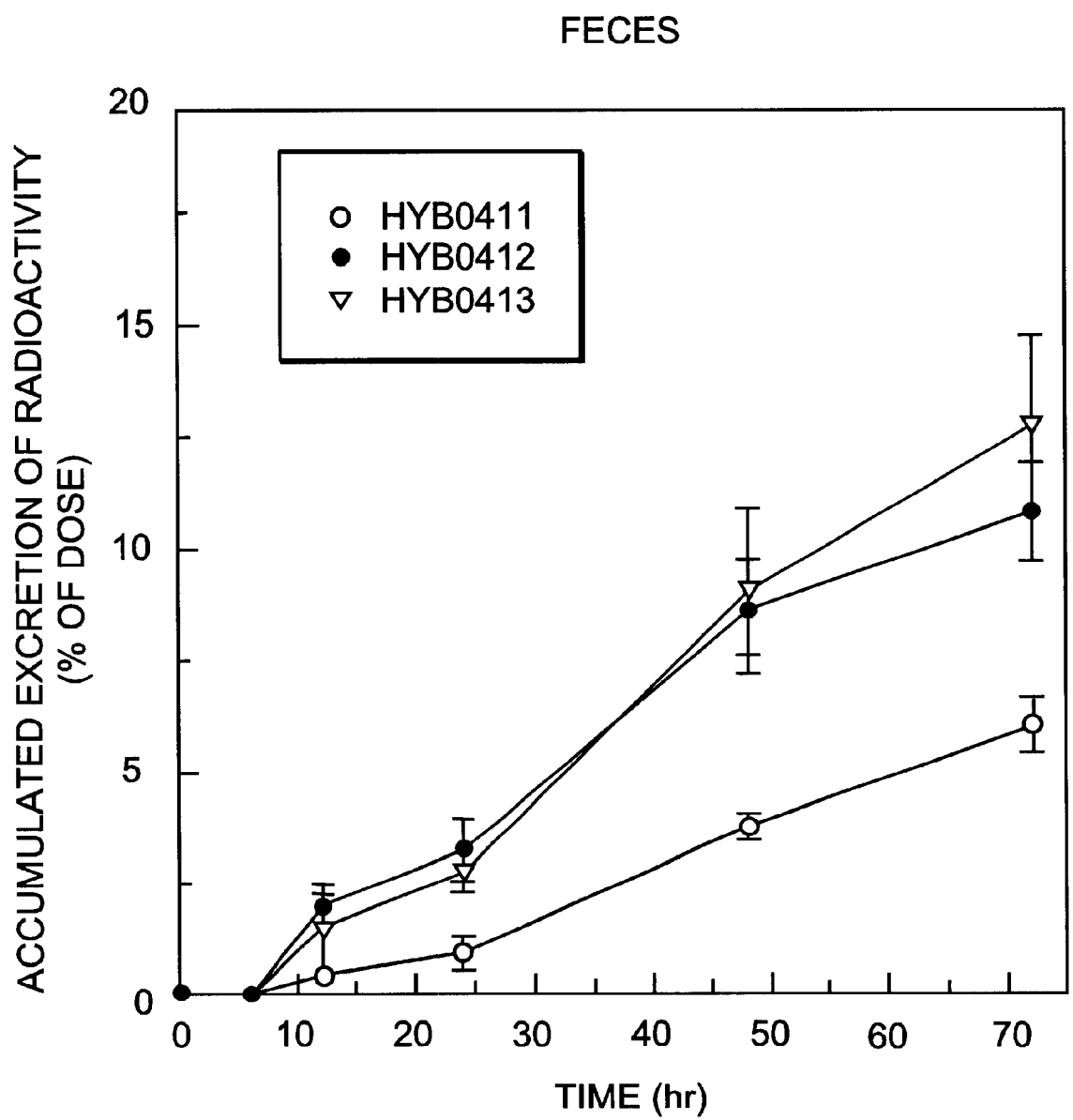
FIG. 10 shows the cumulative excretion of fecal radioactivity over a 48-hour period postinfusion of the radiolabeled bioactive substance according to the present invention.
Figure 11:
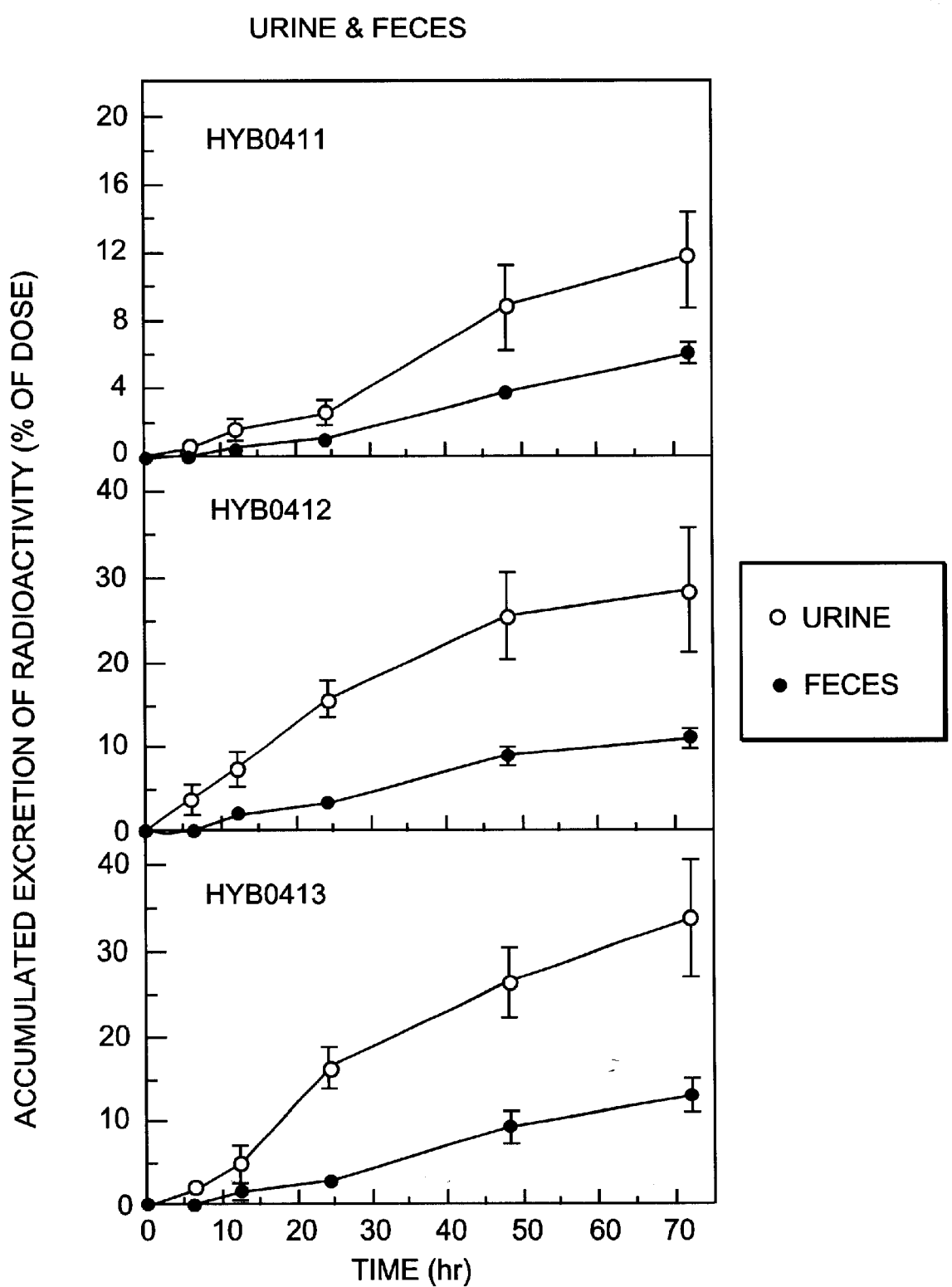
FIG. 11 shows the cumulative excretion of urinary and fecal radioactivity over a 48-hour period postinfusion of radiolabeled Oligonucleotides HYB0411, HYB0412, and HYB0413.

FIGS. 9 and 10 show the cumulative excretion of urinary and fecal radioactivity over 48 hours following administration of radiolabeled oligonucleotides. Urinary excretion represented the major pathway of elimination. Rapid excretion of radioactivity was observed for the first 24 hours following administration (FIGS. 9–10). Oligonucleotide HYB0411 had the lowest urinary excretion rate and Oligonucleotide HYB0413 had the highest urinary excretion rate. Fecal excretion was a minor pathway of elimination (FIG. 11); Oligonucleotide HYB0413 had the highest fecal excretion rate.

Figure 12:
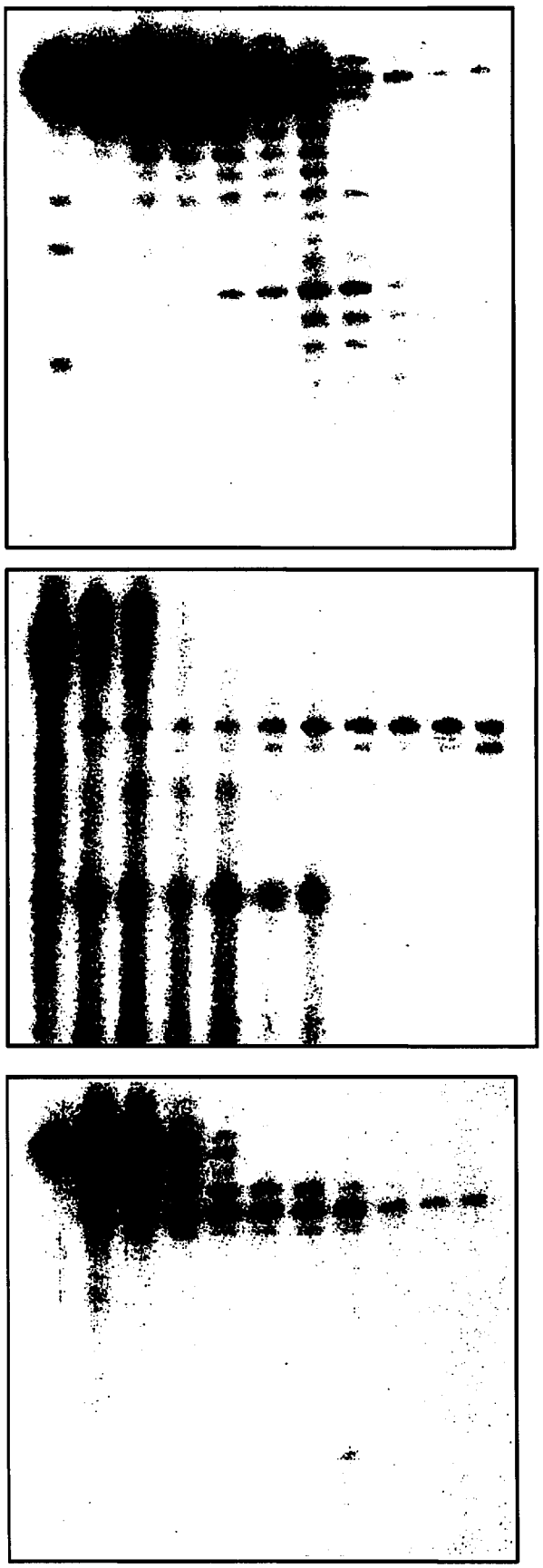
FIG. 12 shows time-dependent degradation of Oligonucleotide HYB0411 as found in kidney tissue.

The chemical forms of radioactivity in tissues were examined by polyacrylamide gel electrophoresis following 5'-post labeling using [$^{32}$P]-ATP and T4 polynucleotide kinase (Agrawal, et al., *Clin. Pharm.* 28:7–16 (1995). As illustrated in FIG. 12, time-dependent degradation of Oligonucleotide HYB0411 was found in the kidney, and a ladder of degradation products were generated. Oligonucleotides HYB0412 showed superior in vivo stability and thus greater absorption than Oligonucleotide HYB0411 due to its ability to form hyperstructures involving contiguous guanosines at the 3'-end.

These experiments show that the bioactive substances according to the present invention have increased in vivo stability, faster plasma clearance, protracted release, and more uniform tissue distribution than the control oligonucleotide counterparts.

What is claimed is:

1. A bioactive substance comprising:
   (a) a hyperstructure forming unit comprising the oligonucleotide sequence GGGG or GTGT at its 3' end;
   (b) an effector unit comprising a nucleotidic portion, which is complementary to a target nucleic acid sequence and does not comprise the sequence GGGG; and
   (c) an operable association between the hyperstructure forming unit and the effector unit.

2. The bioactive substance of claim 1, wherein the effector unit comprises a nucleotidic portion from about 8 to about 100 nucleotides.

3. The bioactive substance of claim 2, wherein the nucleotidic portion of the effector unit has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester; acetamidate, carbamate, thioether, bridged phosphoramidate, bridged methylene phosphonate, bridged phosphorothioate, and sulfone internucleotide linkages.

4. The bioactive substance of claim 2, wherein the nucleotidic portion of the effector unit is chimeric or hybrid, or chimeric and hybrid.

5. The bioactive substance of claim 1, wherein the effector unit comprises a nucleotidic portion from about 12 to about 30 nucleotides.

6. A bioactive substance comprising:
   (a) a hyperstructure forming unit comprising the oligonucleotide sequence GGGG or GTGT at is 3' end;
   (b) an effector unit comprising an amino acid; and
   (c) an operable association between the hyperstructure forming unit and the effector unit.

7. A bioactive substance comprising:
   (a) a hyperstructure forming unit comprising the oligonucleotide sequence GGGG or GTGT at its 3' end;
   (b) an effector unit comprising a lipid; and
   (c) an operable association between the hyperstructure forming unit and the effector unit.

8. A bioactive substance comprising:
   (a) a hyperstructure forming unit comprising the oligonucleotide sequence GGGG or GTGT at its 3' end;
   (b) an effector unit comprising a small molecule drug; and
   (c) an operable association between the hyperstructure forming unit and the effector unit.

9. The bioactive substance of claims 1, 6, 7 or 8, wherein the effector unit is in operable association with two or more effector units.

10. The bioactive substance of claims 1, 6, 7 or 8, wherein the operable association is bioreversible.

11. The bioactive substance of claim 10, wherein the bioreversible operable association comprises an amide, an ester, or a disulfide bond.

* * * * *